(12) United States Patent
Levinson et al.

(10) Patent No.: US 11,001,948 B2
(45) Date of Patent: May 11, 2021

(54) WARP KNIT FABRIC FOR TEXTILE AND MEDICAL APPLICATIONS AND METHODS OF MANUFACTURING THE SAME

(71) Applicants: Duke University, Durham, NC (US); North Carolina State University, Raleigh, NC (US)

(72) Inventors: Howard Levinson, Durham, NC (US); James Brian Davis, Raleigh, NC (US); Don Ward, Mebane, NC (US); Jon Rust, Raleigh, NC (US)

(73) Assignees: Duke University, Durham, NC (US); North Carolina State University, Raleigh, NC (US)

( * ) Notice: Subject to any disclaimer, the term of this patent is extended or adjusted under 35 U.S.C. 154(b) by 86 days.

(21) Appl. No.: 16/308,536

(22) PCT Filed: Jun. 12, 2017

(86) PCT No.: PCT/US2017/037023
§ 371 (c)(1),
(2) Date: Dec. 10, 2018

(87) PCT Pub. No.: WO2017/214620
PCT Pub. Date: Dec. 14, 2017

(65) Prior Publication Data
US 2019/0153640 A1     May 23, 2019

Related U.S. Application Data

(60) Provisional application No. 62/348,211, filed on Jun. 10, 2016.

(51) Int. Cl.
*D04B 21/12*     (2006.01)
(52) U.S. Cl.
CPC .................................. *D04B 21/12* (2013.01)

(58) Field of Classification Search
CPC ........ D04B 21/12; D04B 21/00; D04B 21/02; D04B 21/04; D04B 21/06; D04B 21/08;
(Continued)

(56) References Cited

U.S. PATENT DOCUMENTS

| | | | | |
|---|---|---|---|---|
| 752,033 A | * | 2/1904 | Clewley | .................... D04B 1/22 66/170 |
| 1,139,342 A | * | 5/1915 | Clewley | .................... D04B 1/22 66/170 |

(Continued)

FOREIGN PATENT DOCUMENTS

| | | | | |
|---|---|---|---|---|
| DE | 2503497 A1 | * | 9/1975 | ............. D04B 21/10 |
| DE | 2727218 A1 | * | 12/1978 | ............. D04B 21/10 |

(Continued)

OTHER PUBLICATIONS

"Implantable Material Selection: Nonresorbable Biocompatible Materials: Resorbable Biocompatible Polymers." ATEX, 2016, www.atextechnologies.com/medical-textile-process/improve-innovative-ideas/implantable-material-selection/. (Year: 2016).*

(Continued)

*Primary Examiner* — Khoa D Huynh
*Assistant Examiner* — Grace Huang
(74) *Attorney, Agent, or Firm* — Andrus Intellectual Property Law, LLP

(57) ABSTRACT

A warp knitted fabric formed by a warp knitting machine includes a first knitted portion formed using a first knitting sequence in a machine direction and a formed using a second knitted portion formed using a second knitting sequence in the machine direction, the second knitted portion comprising at least two strips extending in the machine direction, the at least two strips being detached from one another along their lengthwise edges. The second knitted portion has the same width as the first knitted portion, and the first knitted portion (Continued)

and the second knitted portion alternate sequentially in the machine direction and are formed of a single set of continuous textile strands.

20 Claims, 9 Drawing Sheets
(2 of 9 Drawing Sheet(s) Filed in Color)

(58) Field of Classification Search
CPC ...... D04B 21/10; D04B 21/14; D04B 21/145; D04B 21/16; D04B 21/165; D04B 21/18; D04B 21/20; D04B 21/202; D04B 21/205; D04B 21/207; D04B 25/08; D04B 31/00; D04B 31/02
USPC ............ 66/84 R, 85 R, 85 A, 192, 193, 195
See application file for complete search history.

(56) References Cited

U.S. PATENT DOCUMENTS

| | | | | |
|---|---|---|---|---|
| 1,139,343 | A * | 5/1915 | Clewley | D04B 21/18 66/193 |
| 1,803,476 | A * | 5/1931 | Kappler | D04B 1/10 66/85 R |
| 2,233,664 | A * | 3/1941 | Deri | D04B 27/26 66/85 R |
| 2,369,651 | A * | 2/1945 | Amidon | D04B 21/00 66/193 |
| 2,691,286 | A * | 10/1954 | Cooper | D04B 21/10 66/192 |
| 2,992,550 | A | 7/1961 | Frith, Jr. | |
| 3,084,529 | A * | 4/1963 | Scheibe | D04B 21/10 66/193 |
| 4,074,543 | A * | 2/1978 | Schmidt | D04B 21/12 66/193 |
| 4,133,191 | A * | 1/1979 | Blore | D04B 1/104 66/197 |
| 4,215,453 | A * | 8/1980 | Matsuda | A44B 19/34 24/381 |
| 4,497,187 | A * | 2/1985 | Yamaguchi | D04B 21/20 66/196 |
| 4,753,088 | A * | 6/1988 | Harrison | D04B 21/12 2/125 |
| 5,797,283 | A * | 8/1998 | Kaczmarczyk | D04B 21/12 66/193 |
| 5,894,743 | A * | 4/1999 | Bredemeyer | D04B 23/08 66/195 |
| 6,305,875 | B1 * | 10/2001 | Matsumoto | D04B 21/10 405/16 |
| 6,374,643 | B2 * | 4/2002 | Orima | D02G 3/12 66/193 |
| 7,587,915 | B2 * | 9/2009 | Kaneda | D04B 1/26 2/239 |
| 7,775,170 | B2 * | 8/2010 | Zafiroglu | D04B 35/34 112/475.08 |
| 7,892,377 | B2 * | 2/2011 | Lais | D04B 21/10 156/148 |
| 9,884,140 | B2 * | 2/2018 | Shalaby | A61L 27/58 |
| 10,178,991 | B2 * | 1/2019 | Bailly | D04B 21/202 |
| 2001/0042388 | A1 * | 11/2001 | West | D04B 21/02 66/195 |
| 2003/0100954 | A1 | 5/2003 | Schuldt-Hempe et al. | |
| 2004/0049260 | A1 | 3/2004 | Dong | |
| 2008/0208360 | A1 * | 8/2008 | Meneghin | D04B 21/20 623/23.75 |
| 2010/0192638 | A1 | 8/2010 | Wall et al. | |
| 2010/0197999 | A1 | 8/2010 | Deegan et al. | |
| 2011/0130774 | A1 | 6/2011 | Crioscuolo et al. | |
| 2013/0055765 | A1 * | 3/2013 | De Ridder | C03B 35/207 65/348 |
| 2014/0190215 | A1 * | 7/2014 | Schmitz | D04D 7/02 66/190 |
| 2014/0237747 | A1 * | 8/2014 | Torri | D04B 21/04 15/207.2 |
| 2018/0110605 | A1 * | 4/2018 | Couderc | A61F 2/0063 |
| 2019/0309449 | A1 * | 10/2019 | Chikada | D03D 15/0033 |

FOREIGN PATENT DOCUMENTS

| | | | |
|---|---|---|---|
| EP | 1 172 785 | | 1/2002 |
| EP | 1172785 A2 | | 1/2002 |
| EP | 2340769 A2 | | 7/2011 |
| FR | 1319508 A * | 3/1963 | ............ D04B 21/00 |
| GB | 198793 A * | 6/1923 | ............ D04B 9/06 |
| GB | 1284937 A * | 8/1972 | ............ D04B 23/08 |
| GB | 2511484 A | 9/2014 | |
| JP | 02074649 A * | 3/1990 | |

OTHER PUBLICATIONS

Office Action issued Mar. 2, 2020 in counterpart China patent application 201780041014.X.
PCT International Search Report and Written Opinion dated Oct. 31, 2017 in counterpart PCT Application No. PCT/US/17/37023.
European search report dated Jul. 17, 2020 in counterpart European Patent Application 17811156.3.

* cited by examiner

WARP KNIT FABRIC FOR TEXTILE AND MEDICAL APPLICATIONS AND METHODS OF MANUFACTURING THE SAME

CROSS-REFERENCE TO RELATED APPLICATIONS

This patent application is a national stage filing under 35 U.S.C. 371 of International Application No. PCT/US2017/037023, filed Jun. 12, 2017, which claims the benefit of priority of U.S. Provisional Patent Application No. 62/348,211, filed Jun. 10, 2016, both of which are incorporated herein by reference in their entirety.

TECHNICAL FIELD

The present disclosure relates to a warp knit fabric and related methods of manufacturing various embodiments of the warp knit fabric for medical use and for various technical textile applications. In one application, this disclosure relates to an implantable mesh of a Raschel warp knit construction that distributes tensile stress over a larger area between the implantable mesh and the surrounding tissue and, thereby, provides increased durability and better surgical outcomes for patients compared to currently-available devices and methods.

BACKGROUND

Meshes are used in many medical applications, including as implants to repair or restructure tissue, such as skin, fat, fascia, and/or muscle. One common application for such meshes is in hernia repair, such as abdominal wall hernia repairs. A hernia is a protrusion of an organ or tissue through an opening or weakness in the walls that normally retain the organ or tissue within a confined space. Most commonly, hernias occur in the abdominal region; however, hernias may occur in many locations throughout the body, including but not limited to the head, thorax/chest, pelvis, groin, axilla, and upper and lower extremities. Traditionally, there are two main types of surgical hernia repairs: open and laparoscopic hernioplasty. In both types, the hernia defect is closed and reinforced by surrounding tissues.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a warp knitted fabric formed by a warp knitting machine includes a first knitted portion formed using a first knitting sequence in a machine direction, and a second knitted portion formed using a second knitting sequence in the machine direction, the second knitted portion comprises at least two strips extending lengthwise in the machine direction, the at least two strips being detached from one another along their lengthwise edges. The second knitted portion has the same width as the first knitted portion, and the first knitted portion and the second knitted portion alternate sequentially in the machine direction and are formed of a single set of continuous textile strands.

In one embodiment, a method of manufacturing a warp knitted fabric includes knitting a set of textile strands in a first knitting sequence in a machine direction on a warp knitting machine to form a first knitted portion, the first knitted portion having a width, and then knitting the set of textile strands in a second knitting sequence in the machine direction on the warp knitting machine to form a second knitted portion, the second knitted portion having the same width as the first knitted portion. The second knitted portion comprises at least two strips extending lengthwise in the machine direction, wherein the at least two strips are detached from one another along their lengthwise edges. The first knitting sequence and the second knitting sequence are alternately knitted sequentially in the machine direction to form a length of fabric.

In one embodiment, an implantable mesh comprises a mesh body formed using a first knitting sequence in a machine direction, the mesh body having a width. The implantable mesh further includes a first set of two mesh extensions extending parallel to one another in the machine direction from a first side of the mesh body, the at least two mesh extensions formed using a second knitting sequence, wherein the first knitted portion and the second knitted portion are formed continuously from a single set of textile strands.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The present disclosure is described with reference to the following Figures.

DETAILED DESCRIPTION OF THE DRAWINGS

Figure 1:
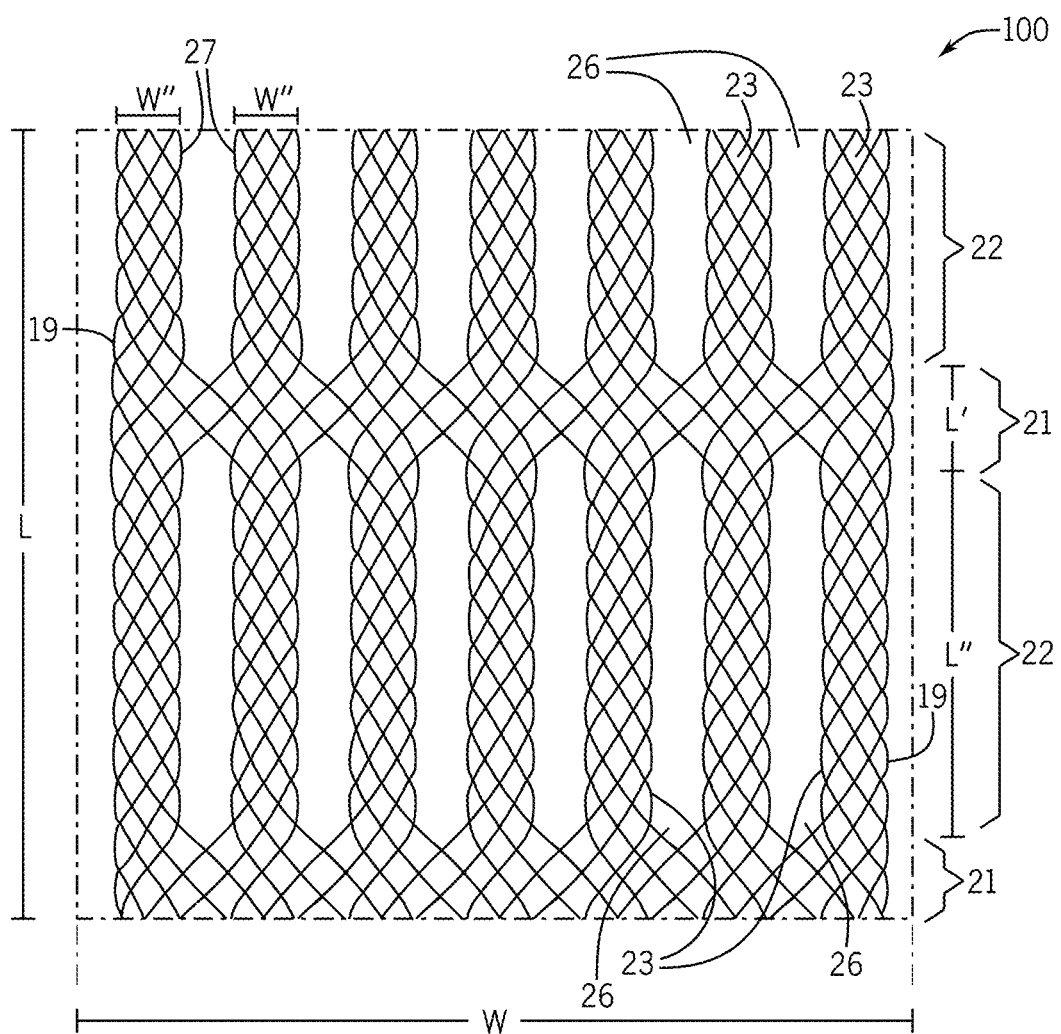
FIG. 1 depicts an exemplary embodiment of a warp knit fabric of the present disclosure.

The current recommendation for ventral hernia repair includes the use of mesh. Various factors contribute to the hernia recurrence; however, the inventors have recognized that failure of the mesh—either through degradation or mechanical failure—remains a significant problem. The inventors have recognized that one source of the problem of hernia repair failures is the construction of the mesh, as prior art meshes are typically a woven piece of material that gets sewn in to the repaired area with sutures. This causes problems, as the material can become unraveled and/or the connections between the sutures and the material can slip. Similar issues occur with other types of mesh or fabric implants.

Upon recognition of the problems and challenges in the relevant field, the inventors developed a warp knit fabric from which an implantable mesh of unitary construction can be created. The implantable mesh of the present disclosure minimizes possible failure points by minimizing the number of separate and/or cut strands in the fabric and by eliminating the need for sutures to fasten the mesh to the affected area. The inventors have further recognized that the developed warp knit fabric has multiple possible embodiments and possible applications, including various medical applications and industrial textile applications. Exemplary industrial textile applications include, but are not limited to, industrial netting for shipping and/or cargo restraint applications, netting for marine or aquatic applications, agricultural and hydroponic applications, or the like.

As illustrated in the figures, the warp knit fabric 100 has two different knitted portions 21 and 22 created using strategically differing knitting sequences, each knitted portion 21 and 22 extending across the width W of the fabric 100. The first knitted portion 21 is formed using a first knitting sequence 31 and the second knitted portion 22 is formed using a second knitting sequence 32, wherein the same textile strands are used in both the first and second sequences 31 and 32. The two knitted portions are alternated in the machine direction along the length L of the fabric 100, and may be alternated at various interval lengths along the fabric as required based on the particular application of use for the fabric 100. Whereas the first knitted portion 21 is constructed to form a fabric portion that is continually connected across the width W, the second knitted portion 22 is characterized by forming at least two strips 23 extending parallel and lengthwise in the machine direction. The strips 23 are detached from one another along their lengths L", such that the fabric 100 has slits 26 or holes between the strips 23 and that run the length L" of the strips 23, which is approximately or nearly the length of the second knitted portion 22.

The strips 23 extend from the first knitted portion 21 and may generally continue the knitting sequence, or pattern, of the first knitted portion 21, with only a change in the pattern along the lengthwise edges 27 of the strips 23. Thus, portions of the second knitting sequence 32 may be the same as the first knitting sequence 31—i.e., the pattern executed by certain guide bars may remain the same for both the first knitting sequence 31 and the second knitting sequence 32 (FIGS. 2B-2C). Thus, a middle portion 28 of the strips 23 (see FIG. 3) may continue the same pattern used for the first knitted portion 21 in an uninterrupted fashion. In certain embodiments, the only change made in transitioning between the first knitting sequence 31 and the second knitting sequence 32 (and vice versa) is with respect to the guide bars knitting the lengthwise edges 27 of the strips 23. In one embodiment, the first knitting sequence 31 differs from the second knitting sequence 32 for only a number of guide bars necessary to create the strips 23. Thus, any guide bar executing a pattern that crosses over the slits 26 between the strips 23 is changed. Further, the number of textile strands 17 that change is dependent on the number of strips 23 in the second knitted portion 22.

Since the warp knit fabric 100 is knitted from a single set of textile strands, and the strands are not cut anywhere along their lengths, the disclosed fabric 100 has excellent durability and avoids fraying or failures, including at the juncture between the knitted portions 21 and 22 where the warp knit fabric 100 changes from having a unitary width to forming two or more strips 23. Depending on the intended application of use, the disclosed warp knit fabric 100 may be constructed using any number of warp knitting patterns, or sequences, using any type of textile strand, including any filament, filament yarn (including single filament or multifilament yarns), or spun yarn. Likewise, the textile strands may be of a synthetic or natural material. For example, in certain embodiments of the warp knit fabric 100 for medical applications, the textile strands 17 may be of a synthetic biocompatible material such as, but not limited to, polypropylene, polyethylene terephthalate polyester, expanded polytetrafluroethylene (ePTFE), polyglactin, polyglycolic acid, trimethylene carbonate, poly-4-hydroxybutyrate (P4HB), polyglycolide, polyactide, and trimethylene carbonate (TMC). In other embodiments, the textile strands 17 may be from biocompatible and biological materials, including, but not limited to, human dermis, porcine dermis, porcine intestine, bovine dermis, and bovine pericardium. The textile strands 17 may also comprise a combination of synthetic and biologic materials.

Figure 6A:
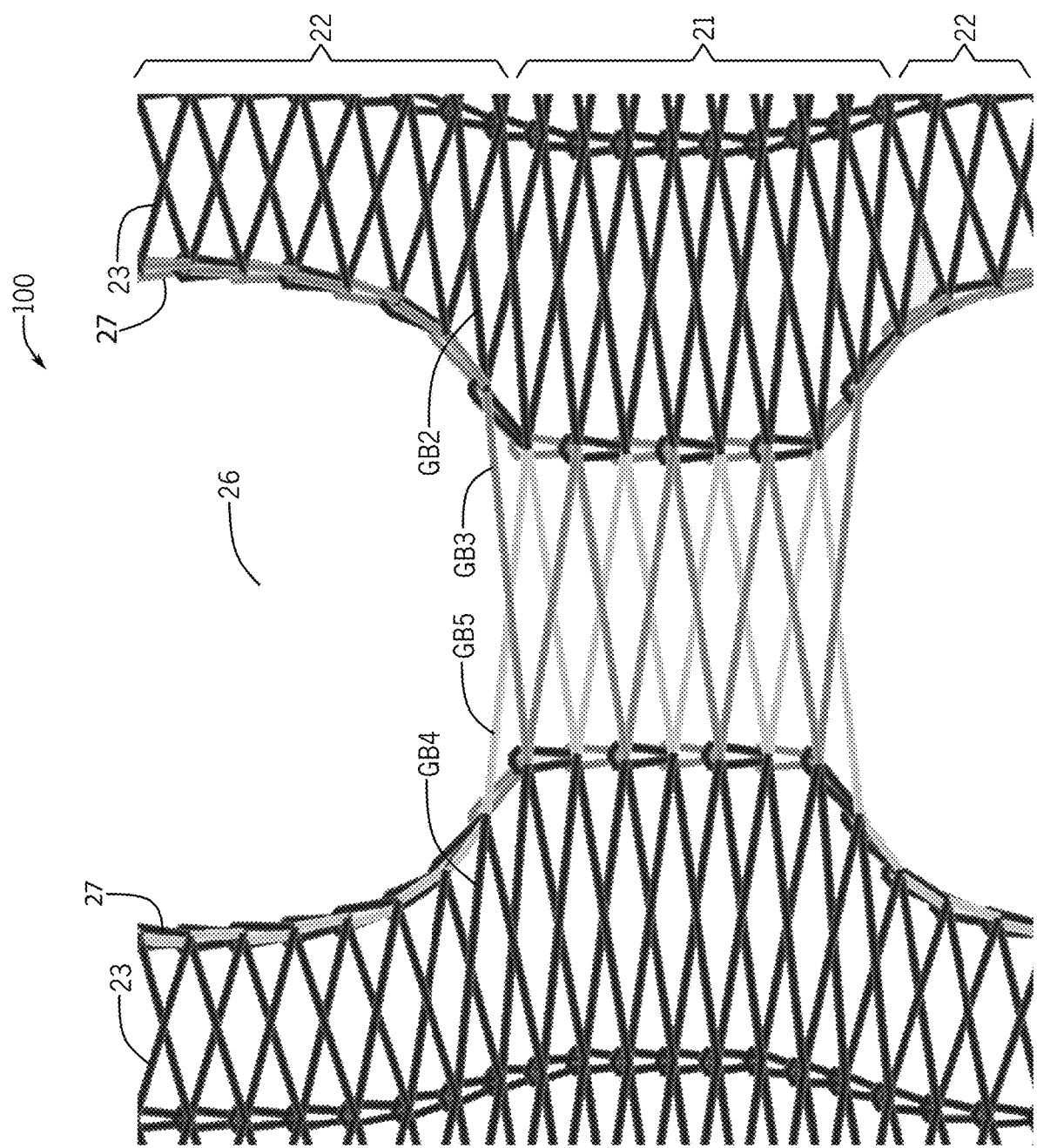
FIGS. 6A-6C depict another exemplary knitting sequence for manufacturing another embodiment of the warp knit fabric of the present disclosure.
Figure 6B:
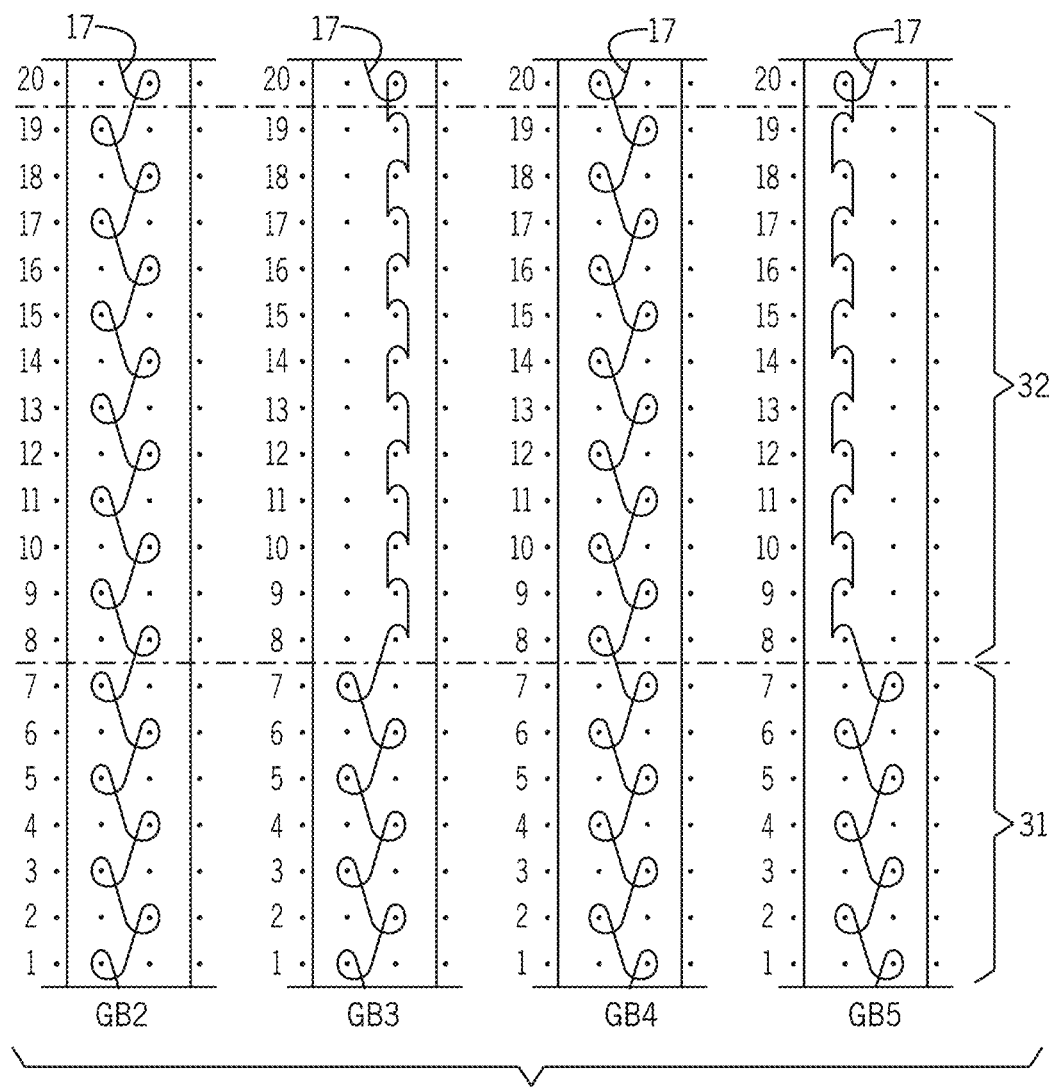
Figure 6C:
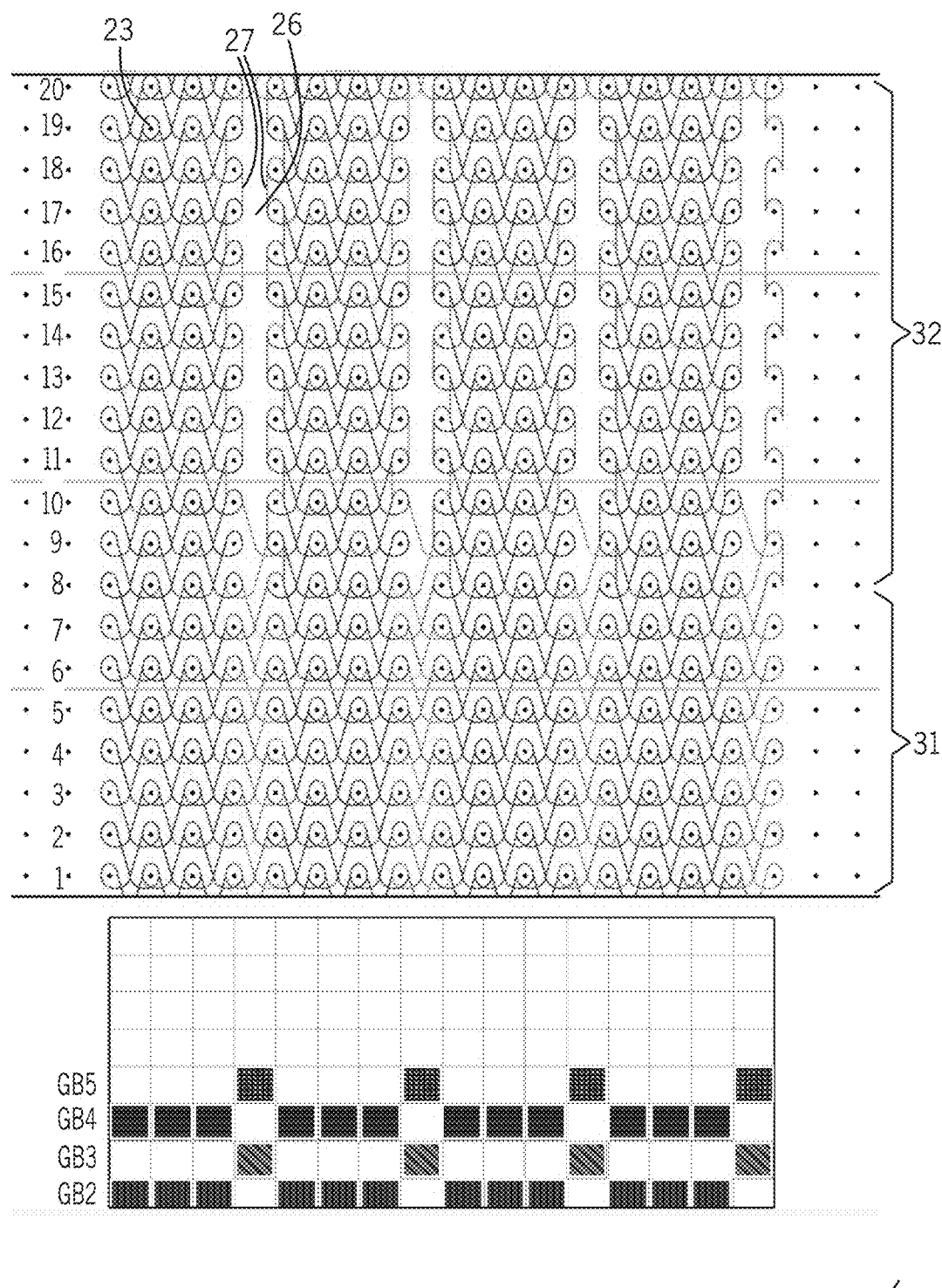

The warp knit fabric 100 may be a tightly knitted, solid-looking fabric, or may be an openwork knit, such as a mesh, having openings, or pores, throughout. FIGS. 1-3 exemplify one embodiment of the warp knit fabric 100 being an openwork mesh having diamond-shaped openings. FIGS. 6A-6C exemplify another embodiment of the warp knit fabric 100 wherein different knitting sequences are used to form the first and second knitted portions 21 and 22. Any of various other embodiments are possible, and the knitting patterns shown are merely exemplary ways of forming the first and second knitted portions 21 and 22, wherein the second knitted portion comprises two or more strips.

Referring to FIG. 1, the warp knit fabric 100 is shown wherein the first knitted portion 21 is relatively short lengthwise compared to the length L" of the second portion 22 comprising the strips 23. The fabric has a width W, and both the first knitted portion 21 and the second knitted portion 22 span, or at least approximately span, that same width W. In the depicted embodiment, the second knitted portion 22 comprises seven strips 23, wherein each strip has the same width, represented as W". In other embodiments, the second knitted portion 22 may be formed by any number of two or more strips 23, such as three strips, four strips, five strips, and so on. For example, the second knitted portion 22 may be divided into just two strips, and therefore having just one slit 26 in each second knitted portion 22 of the warp knit fabric 100. The strips may be any width W" that is less than the width W. The strips may be of equal widths W" to one another, or the widths of the strips 23 may vary across the fabric. FIG. 3 provides an example wherein the second knitted portion 22 comprises strips 23 having varying widths, including narrower strips of width $W_1$" and wider strips of width $W_2$".

The lengths of the respective first and second knitted portion 21 and 22 may vary. In the embodiment of FIG. 1, the length L' of the first knitted portion 21 is comparatively shorter than the length L" of the second knitted portion 22. However, the lengths L and L' may be any value and any proportion with respect to one another. Thus, in other embodiments, the length L' of the first knitted portion 21 may be comparatively longer than the length L" of the second knitted portion 22, or the lengths L' and L" of the first and second knitted portions 21 and 22 may be the same. Similarly, the lengths L' and L" may be varied along the length L of the entire fabric.

Figure 2A:
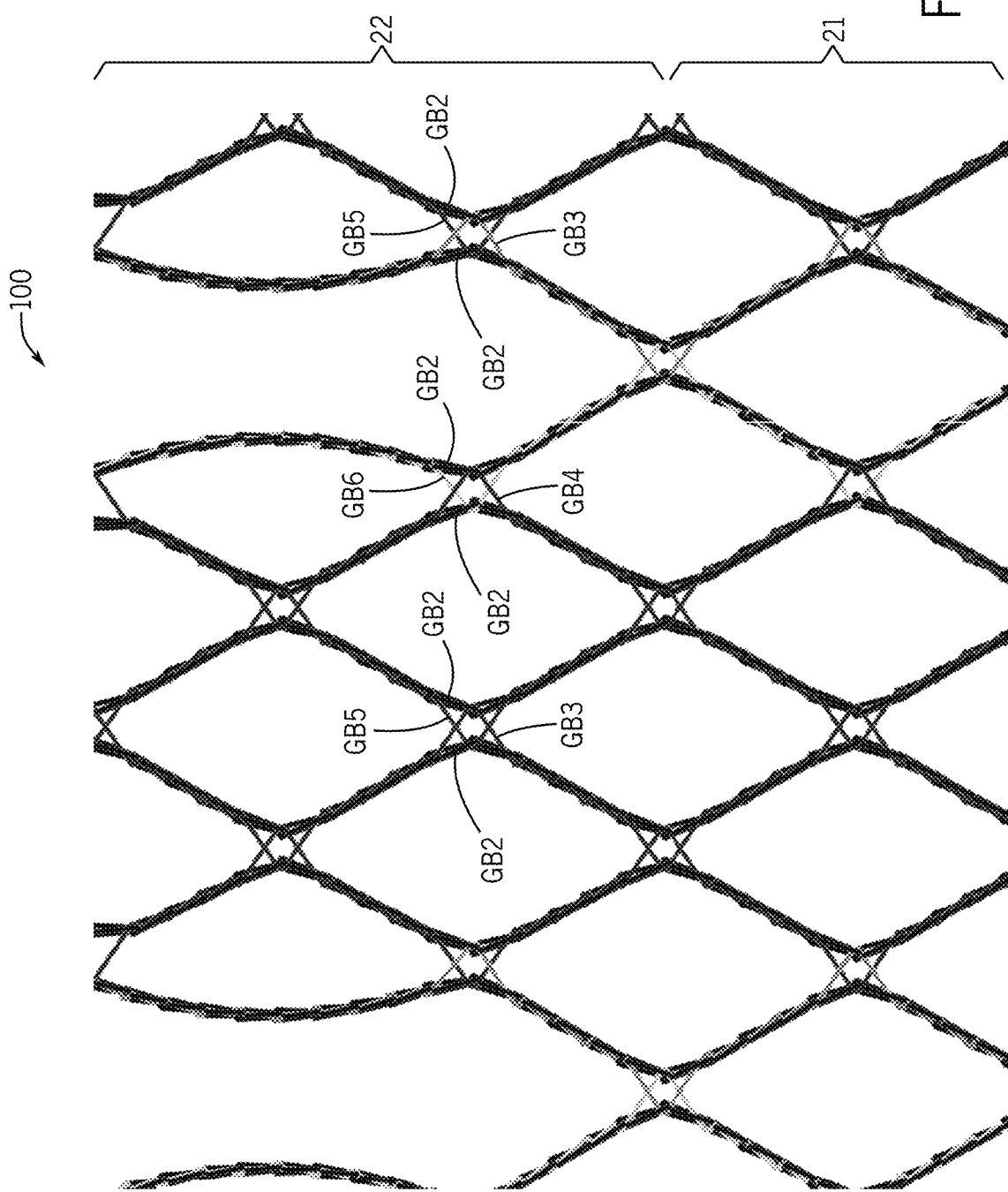
FIGS. 2A-2C depict exemplary knitting sequences that may be implemented to manufacture the embodiment of FIG. 1.
Figure 2B:
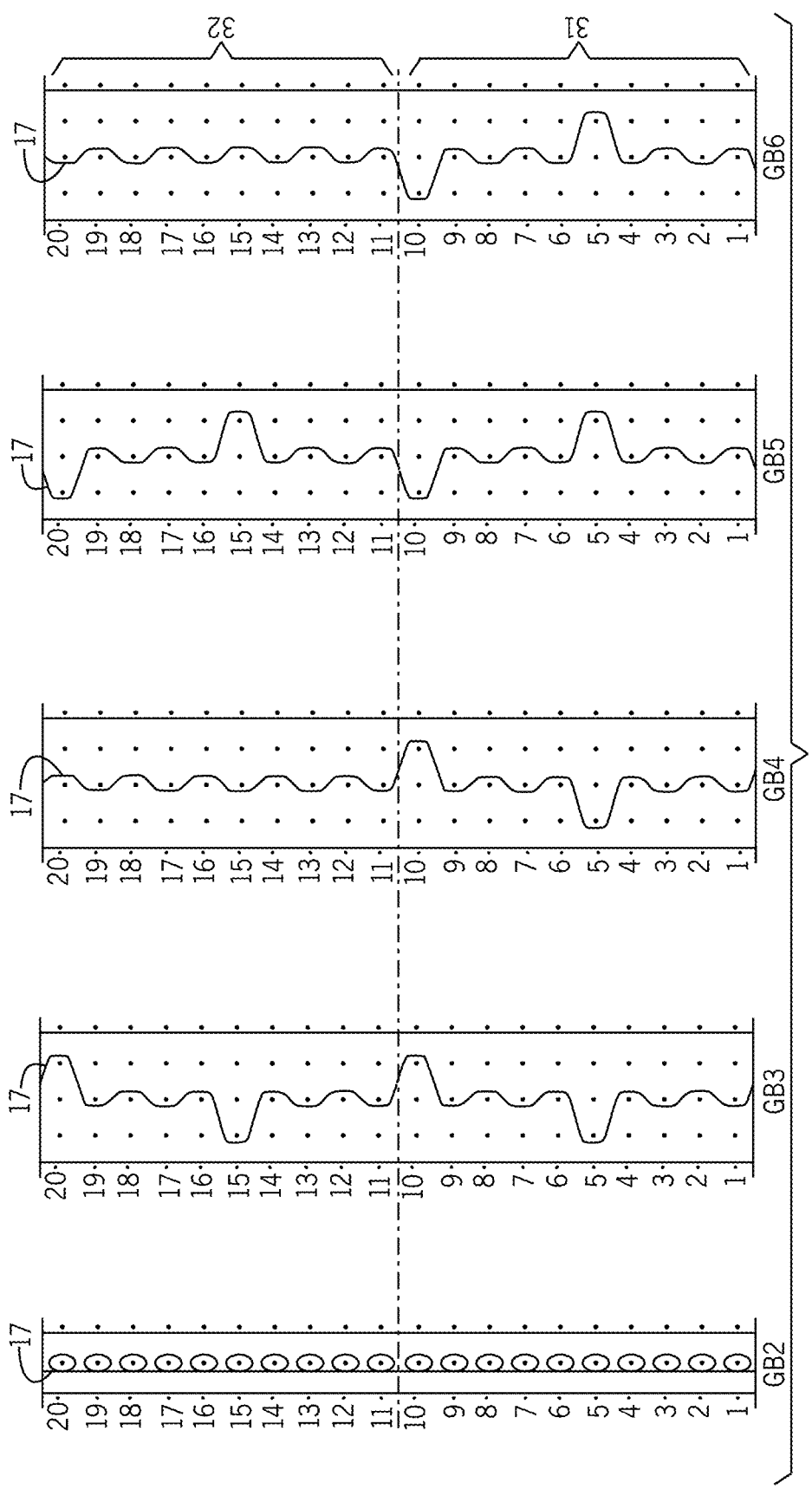
Figure 2C:
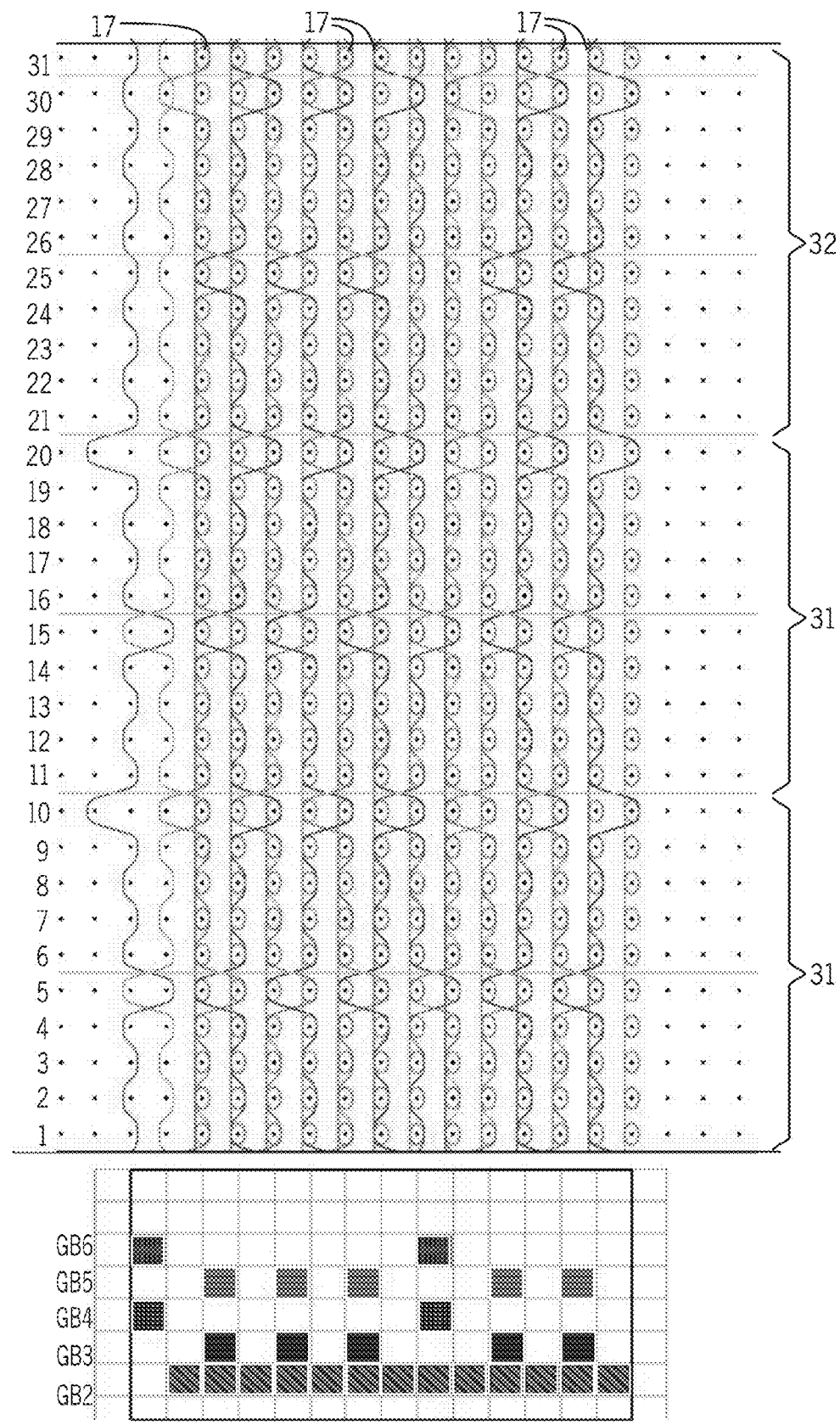
Figure 3:
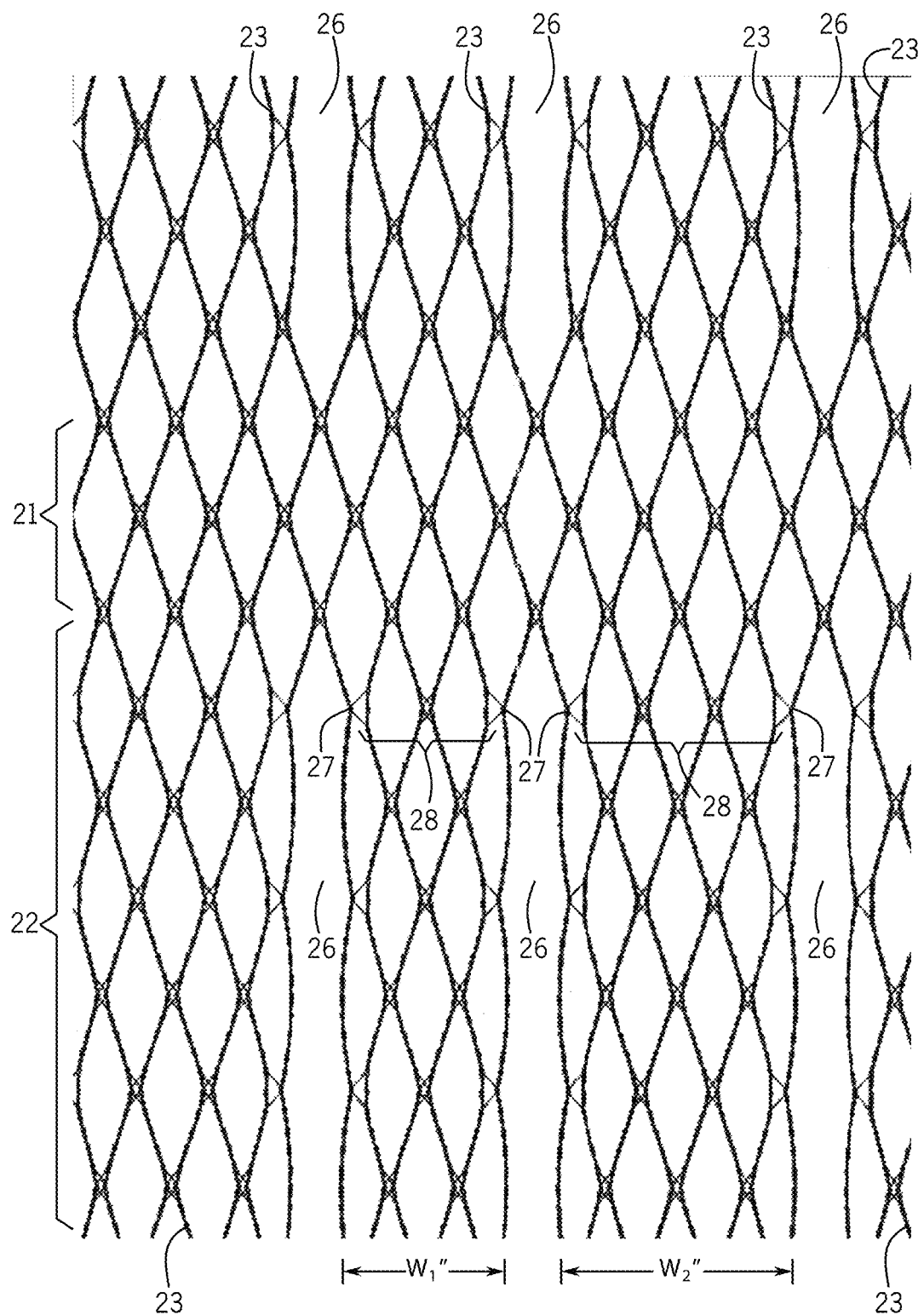
FIG. 3 depicts another embodiment of a warp knit fabric manufactured using the knitting sequences depicted in FIGS. 2A-2C.

FIGS. 2A-2C exemplify knitting sequences that may be used to form the exemplary embodiment of FIG. 1. The exemplary embodiment shown in FIGS. 2A-2C is constructed using a Raschel warp knitting machine having at least four guide bars. The exemplary embodiment shown in FIGS. 6A-6C is also constructed using a Raschel warp knitting machine having at least four guide bars. For example, embodiments may be knitted on a single needle bar or a double needle bar Raschel warp knitting machine, or a tricot knitting machine. In certain embodiments, an electronic guide bar control machine may be preferable because of the length of the two alternating knitted portions. The warp knitting machine is configured to alternate between the depicted first knitting sequences 31 and second knitting sequences 32 at predetermined intervals.

FIGS. 2B-2C are sequence diagrams depicting the first knitting sequence 31 and the second knitting sequence 32, each of which may be repeated any number of times in the machine direction before transitioning to the other knitting sequence. For example, in FIG. 2C the first knitting sequence 31 is repeated twice, and then the second knitting sequence follows, such as for eight repetitions. Each knitting sequence 31, 32 includes a repeatable ten-stitch pattern involving five guide bars (GB2 through GB6). FIG. 2B depicts the sequence for each guide bar GB2 through GB6. As can be seen from FIGS. 2B and 2C, the first knitting sequence 31 and the second knitting sequence 32 are the same for three of the five guide bars. GB2, GB3, and GB5 execute the same pattern in both the first knitting sequence 31 and the second knitting sequence 32. The pattern changes for two of the guide bars, GB4 and GB6. Namely, in the first knitting sequence 31, GB4 and GB6 cross over a neighboring needle every fifth stitch in order to connect, or create joints, with the strands in the neighboring row. This forms the mesh connections across the width of the mesh. In the second knitting sequence 32, the cross connections made by guide bars GB4 and GB6 are dropped and the stitch stays on the same needle row for the length of the second knitting sequence 32.

FIG. 2C provides another diagram showing the knitting sequences 31 and 32 showing repetition of the guide bar stitch patterns. In various embodiments, the stitches created by each guide bar may be repeated any number of times to create any width W of fabric 100. Moreover, the edge stitch may vary from that shown, depending on how the edge is finished. As shown in the embodiment of FIG. 1, the fabric edge 19 may be formed by a constant and continuous stitch sequence that remains the same for the first knitted portion 21 and the second knitted portion 22, which may be the same or similar stitch sequence as used to form the lengthwise edges 27 of the strips 23.

The color ledger at the bottom of FIG. 2C corresponds to the stitching sequences shown above, where the colored boxes in the guide bar ledger vertically align with and indicate the presence of the stitch in the needle rows above the ledger. The textile strands on guide bar GB2 are shown in green, those on guide bar GB3 are shown in dark blue, those on guide bar GB4 are shown in yellow, those on guide bar GB5 are indicated in light blue, and those on guide bar GB6 are indicated in purple. These colors are shown in the ledger as colored boxes with differential hatching also indicating the color. For clarity, the left-most portion of FIG. 2C shows the textile strands 17 of only guide bars GB4 and GB6 separated from the textile strands on guide bar GB2 so that the pattern executed by guide bars GB4 and GB6 can be seen more clearly (because that portion changes between the first knitting sequence 31 and the second knitting sequence 32). It will be understood by a person having ordinary skill in the art that in actual implementation, the textile strands on guide bars GB4 and GB6 would each interlace with textile strands following the pattern on guide bar GB2, but that guide bar GB2 is not shown on the two left-most rows for clarity purposes so that aspect of the sequences 31 and 32 are more visible.

FIG. 3 depicts another embodiment, or execution of the first and second knitting sequences. In the depicted embodiment, the second knitted portion 22 includes strips 23 of varying widths $W_1''$ and $W_2''$, and the second knitting sequence is repeated sequentially for a predetermined number of times (which in the depicted embodiment is at least three repetitions), whereas the first knitting sequence 21 is repeated only twice before returning to the second knitting sequence 32. Thus, the length of the first knitted portion 21 is much shorter than the second knitted portion 22 having the strips. As described above, this relationship of lengths can be changed such that the first knitted portion 21 and the second knitted portion 22 have any length and are repeated at any interval with respect to one another.

Figure 4:
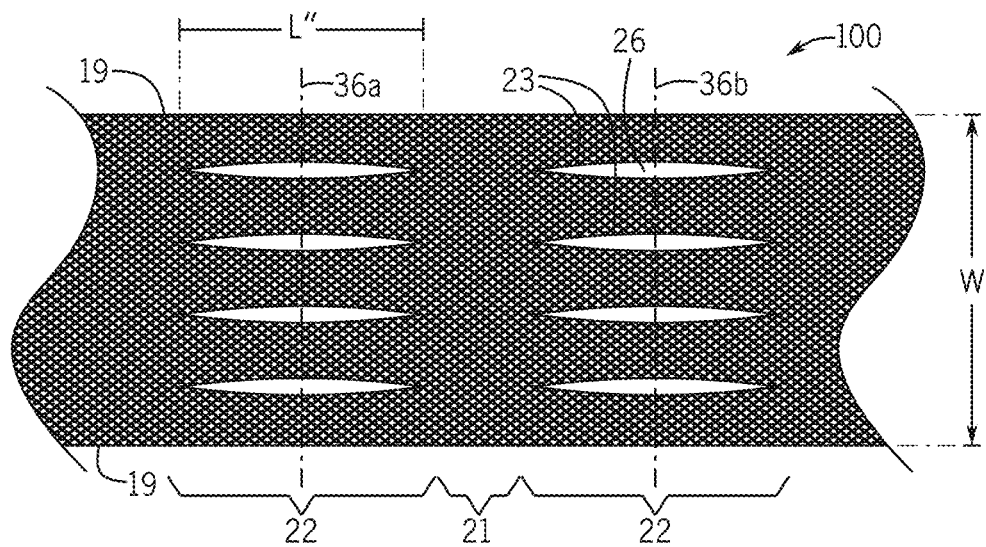
FIG. 4 depicts another embodiment of the warp knit fabric.

FIG. 4 depicts a portion of the warp knit fabric 100 showing an alternating sequence of the first knitted portion 21 and the second knitted portion 22. As described above, the fabric may be used for any number of medical, industrial, and/or technical textile applications. In one embodiment, the warp knit fabric 100 may be used as an implantable mesh 1. Namely, the strips 23 may be used to form mesh extensions 3 extending from a mesh body 7, which is formed by the first knitted portion 21. The strips may be cut width-wise to form a mesh piece having a mesh body formed by the first knitted portion and two sets of at least two extensions, each set of at least two extensions formed by respective second knitted portions on either side of the first knitted portion. The warp knit fabric 100 may be cut along its width W to form individual implantable fabric mesh pieces, or mesh implants, that are biocompatible and surgically implantable in a patient, such as that shown in FIG. 4. In the embodiment of FIG. 4, dashed lines 36a and 36b show exemplary cut locations where the warp knit fabric 100 may be cut to create an implantable mesh 1, an embodiment of which is shown in FIG. 5.

Figure 5:
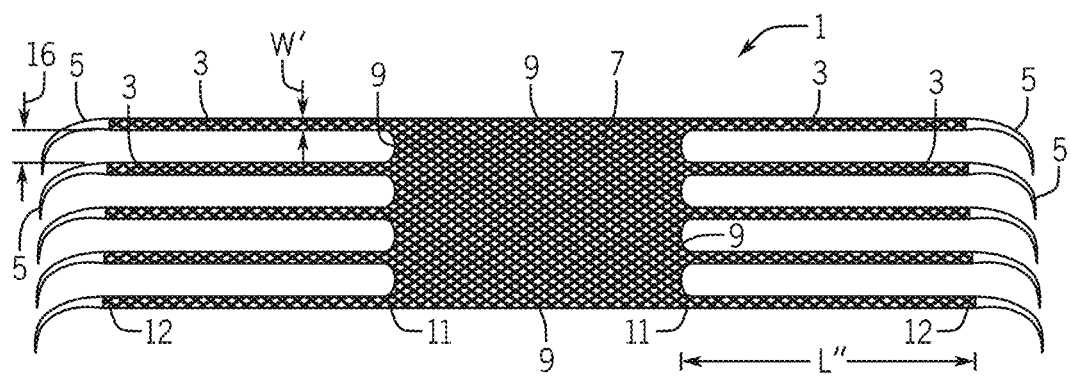
FIG. 5 depicts one embodiment of an implantable mesh comprising the warp knit fabric.

FIG. 5 depicts one embodiment of an implantable mesh 1 comprising the warp knit fabric 100. The implantable mesh 1 has a mesh body 7 and multiple mesh extensions 3 extending from opposing sides of the mesh body 7. At the end of each mesh extension 3 is a fixation device 5, which in the depicted embodiment is a surgical needle. Each mesh extension 3 has a first end 11 that is part of and extends from the mesh body 7. Each mesh extension 3 also has a second end 12 that attaches to the fixation device 5. Each mesh extension 3 has a length L" between the first end 11 and the second end 12 and a width W".

The implantable mesh is formed by cutting the fabric 100 widthwise along the second knitted portion 22, such as along dashed lines 36a and 36b. For example, cuts may be made across the entire width W of the fabric 100, thereby cutting each of the strips 23. For example, the cuts may be made half way along the length L" of each second knitted portion 21, such as with a heated knife so that the ends 12 of each extension do not fray. Thereby, the fabric 100 is cut into several implantable meshes 1.

The mesh body 7 has a surrounding edge 9 from which the mesh extensions 3 extend. At least two mesh extensions 3 extend from the mesh body 7, and, in various embodiments, the implantable mesh 1 may have any number of additional mesh extensions 3. In the embodiment of FIG. 5, the implantable mesh 1 has ten mesh extensions 3 arranged in opposing pairs extending oppositely from surrounding edges 9 of the mesh body 7. In FIG. 5, the mesh extensions 3 extend from only two of the surrounding edges 9.

The mesh extensions 3 of the implantable mesh 1 have sufficient length L' to permit multiple anchor points with surrounding tissue upon implantation. An anchor point is a position where the mesh extension passes through some portion of the surrounding tissue in order to provide a force against migration or dehiscence. Multiple anchor points refers to more than one anchor point. For example, each mesh extension 3 may be passed through the surrounding tissue multiple times, such as by weaving or sewing the mesh extensions 3 into the tissue with the fixation device 5. Additionally, in some embodiments the distal end 12 of the mesh extension 3 may be secured to bone. Thereby, the implantable mesh 1 of the present disclosure is configured such that, upon implantation, it can withstand substantial forces, including tensile stress, without failure. This device and implantation method is especially applicable for providing a durable reconstruction or repair of a tissue defect, such as a repair of an abdominal hernia or a breast reconstruction.

A properly implantable mesh 1 is able to withstand increased tensile stress compared to prior art devices that are sutured to surrounding tissue by conventional anchoring methods. One force distribution mechanism at play is frictional resistance, which is distributed across numerous points of contact between the implantable mesh 1 and the surrounding tissue. The amount of frictional resistance between the implantable mesh 1 and the tissue may depend on numerous factors, including, but not limited to, the area over which the tensile stress is distributed, forces that press the mesh into the tissue, the relative roughness of the mesh and the tissue, the method of fixation, and the extent of bioincorporation of the mesh into the tissue. As long as frictional resistance exceeds tensile stress at each of the anchor points, or points of contact, the mesh will not migrate or dehisce.

In an exemplary embodiment, the length L' of the mesh extensions 3 is at least 10 cm. In another embodiment, the length L" of the mesh extensions 3 is at least 16 cm, 18 cm or 20 cm long and may be up to 25, 30, 35 or 40 cm long; and in still other embodiments the mesh extensions 3 may be even longer than 40 cm to allow for fixation to certain tissues or for the distal end 12 of the mesh extension 3 to be fixed to bone. However, in certain applications, the mesh extensions may be less than 10 cm, such as where the implantable mesh 1 is small and/or intended for repair or reconstruction of tissue that does not withstand significant forces. The mesh extensions 3 of the implantable mesh do not need to all be the same length. In one embodiment, at least one mesh extension is at least 18, 20 or 22 cm long, but the implantable mesh may include additional mesh extensions that are less than 18 cm long or longer than 22 cm long.

The mesh extensions 3 may have any of various widths. For the embodiment of FIG. 5, the width W" of each mesh extension 3 may be between 0.2 cm and 3 cm, or more. For example, experimentation and research by the inventor relating to abdominal hernia repairs has revealed that mesh extensions 3 having a width W" between 0.5 cm and 2 cm are advantageous and provide desirable durability results for use in hernia repair, which include mesh extensions 3 having a width W" of 0.5 cm, 0.75 cm, and 1 cm. It will be understood by one of skill in the art that any number of extensions 3 having a wide variety of widths W" are possible, and that the number of extensions 3 will depend on the widths W" of each extension and the overall width W of the fabric 100.

In FIG. 5, the implantable mesh 1 is depicted as including ten mesh extensions 3 with five mesh extensions 3 extending from the surrounding edge 9 on opposite sides of the mesh body 7. As noted above, the mesh extensions 3 may extend from one or more of the surrounding edges 9 of the mesh body 7. In addition, various embodiments may include various numbers of mesh extensions 3. For example, the implantable mesh may include two, three, four, five, six, seven, ten, twelve, fourteen or even more mesh extensions. The number and width of mesh extensions required may depend on characteristics known to those skilled in the art, such as the size and placement of the tissue defect or reconstruction site and the availability or proximity of the surrounding tissue to the tissue defect or site of reconstruction.

FIGS. 6A-6C depict another exemplary embodiment of first and second knitting sequences 31 and 32 that may be used to form the fabric 100. As shown in FIGS. 6B and 6C, the first and second knitting sequences 31 and 32 generally employ four guide bars GB2-GB5. The stitch pattern formed by two of the guide bars, GB2 and GB4, remains the same between the first knitting sequence 31 and the second knitting sequence 32. The stitch pattern of the remaining two guide bars, GB3 and GB5, changes from the first knitting sequence 31 to the second knitting sequence 32. Namely, the stitch patterns executed on guide bars GB3 and GB5 go from alternating back and forth between two adjacent needle rows in the first knitting sequence 31, to stitching only along a single needle row in the second knitting sequence 32. Thereby, GB3 and GB5 form lengthwise edges 27 of respective strips 23, which is shown in FIGS. 6A and 6C. FIG. 6C provides a color coded picture of the knitting sequences 31 and 32, showing repetition of the guide bar stitch patterns across the width of the fabric. These colors are shown in the ledger as color boxes with differential hatching also indicating the color. In various embodiments, the stitches created by each guide bar may be repeated any number of times to create any width W of fabric 100. The color ledger at the bottom of FIG. 6C corresponds to the stitching sequences shown above, where the colored boxes in the guide bar ledger vertically align with and indicate the presence of the stitch in the needle rows above the ledger. The textile strands on guide bar GB2 are shown in red, those on guide bar GB3 are shown in green, those on guide bar GB4 are shown in blue, and those on guide bar GB5 are shown in yellow. As illustrated, the change on guide bars GB2 and GB3 between the first knitting sequence 31 and the second knitting sequence 32 creates the strips 23 in the second knitted portion. Thus, slits are formed between adjacent stitches formed by guide bars GB3 and GB5, which form lengthwise edges 27 of respective strips 23.

The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

The invention claimed is:

1. A warp knitted fabric formed by a warp knitting machine, the warp knitted fabric comprising:

a first knitted portion formed using a first knitting sequence in a machine direction, the first knitted portion having a width and wherein the first knitting sequence comprises the following:
GB2 (3–2/3–2/3–2/3–2/3–2/3–2/3–2/3–2/3–2/3–2)//
GB3 (2–2/1–1/2–2/1–1/3–3/1–1/2–2/1–1/2–2/0–0)//
GB4 (2–2/1–1/2–2/1–1/3–3/1–1/2–2/1–1/2–2/0–0)//
GB5 (2–2/3–3/2–2/3–3/1–1/3–3/2–2/3–3/2–2/4–4)//
GB6 (2–2/3–3/2–2/3–3/1–1/3–3/2–2/3–3/2–2/4–4)//:
a second knitted portion formed using a second knitting sequence in the machine direction, the second knitted portion comprises at least two strips extending lengthwise in the machine direction, the at least two strips being detached from one another along their lengthwise edges, and wherein the second knitting sequence comprises the following:
GB2 (3–2/3–2/3–2/3–2/3–2/3–2/3–2/3–2/3–2/3–2)//
GB3 (2–2/1–1/2–2/1–1/3–3/1–1/2–2/1–1/2–2/0–0)//
GB4 (2–2/1–1/2–2/1–1/2–2/1–1/2–2/1–1/2–2/1–1)//
GB5 (2–2/3–3/2–2/3–3/1–1/3–3/2–2/3–3/2–2/4–4)//
GB6 (2–2/3–3/2–2/3–3/2–2/3–3/2–2/3–3/2–2/3–3)//
wherein second knitted portion has the same width as the first knitted portion;
wherein the first knitting sequence is repeated at least twice to form the first knitted portion and the second knitting sequence is repeated at least twice to form the second knitted portion; and
wherein the first knitted portion and the second knitted portion alternate sequentially in the machine direction and are formed of a set of continuous textile strands.

2. The warp knitted fabric of claim 1, wherein the first knitting sequence and the second knitting sequence are identical for at least two guide bars and differ for at least two guide bars.

3. The warp knitted fabric of claim 1, wherein the second knitting sequence is identical to the first knitting sequence except at the lengthwise edge of each strip.

4. The warp knitted fabric of claim 1, wherein the second knitting sequence only differs from the first knitting sequence for two guide bars.

5. The warp knitted fabric of claim 1, wherein the warp knitted fabric is formed on a Raschel warp knitting machine having at least five guide bars.

6. The warp knitted fabric of claim 1, wherein the first knitted portion and the second knitted portion comprise a Raschel warp knit mesh with diamond-shaped openings.

7. The warp knitted fabric of claim 1, the second knitted portion having at least three, at least four or at least five parallel strips extending in the machine direction.

8. The warp knitted fabric of claim 1, wherein each strip has a width not greater than 2 cm.

9. The warp knitted fabric of claim 1, wherein the textile strands are synthetic multi-filament yarn, synthetic single-filament or spun yarn.

10. The warp knitted fabric of claim 1, forming a biocompatible implantable mesh for use in reconstructing tissue.

11. A method of manufacturing a warp knitted fabric, the method comprising:
knitting a set of textile strands in a first knitting sequence in a machine direction on a warp knitting machine to form a first knitted portion, the first knitted portion having a width and wherein the first knitting sequence comprises the following:
GB2 (3–2/3–2/3–2/3–2/3–2/3–2/3–2/3–2/3–2/3–2)//
GB3 (2–2/1–1/2–2/1–1/3–3/1–1/2–2/1–1/2–2/0–0)//
GB4 (2–2/1–1/2–2/1–1/3–3/1–1/2–2/1–1/2–2/0–0)//
GB5 (2–2/3–3/2–2/3–3/1–1/3–3/2–2/3–3/2–2/4–4)//
GB6 (2–2/3–3/2–2/3–3/1–1/3–3/2–2/3–3/2–2/4–4)//
knitting the set of textile strands in a second knitting sequence in the machine direction on the warp knitting machine to form a second knitted portion, the second knitted portion having the same width as the first knitted portion; and wherein the second knitting sequence comprises the following:
GB2 (3–2/3–2/3–2/3–2/3–2/3–2/3–2/3–2/3–2/3–2)//
GB3 (2–2/1–1/2–2/1–1/3–3/1–1/2–2/1–1/2–2/0–0)//
GB4 (2–2/1–1/2–2/1–1/2–2/1–1/2–2/1–1/2–2/1–1)//
GB5 (2–2/3–3/2–2/3–3/1–1/3–3/2–2/3–3/2–2/4–4)//
GB6 (2–2/3–3/2–2/3–3/2–2/3–3/2–2/3–3/2–2/3–3)//
wherein the first knitting sequence is repeated at least twice to form the first knitted portion and the second knitting sequence is repeated at least twice to form the second knitted portion:
wherein the second knitted portion comprises at least two strips extending lengthwise in the machine direction, the at least two strips being detached from one another along their lengthwise edges; and
alternately knitting the first knitting sequence and the second knitting sequence sequentially in the machine direction.

12. The method of claim 11, wherein the first knitting sequence and the second knitting sequence differ for at least two guide bars.

13. The method of claim 11, wherein the first knitting sequence and the second knitting sequence are the same for at least one guide bar.

14. The method of claim 11, wherein the warp knitted fabric is formed on a Raschel warp knitting machine having at least five guide bars.

15. The method of claim 11, wherein the first knitted portion and the second knitted portion comprise a Raschel warp knit mesh with diamond-shaped openings.

16. The method of claim 11, the second knitted portion having at least three or at least four strips extending in the machine direction.

17. The method of claim 11, wherein the textile strands are synthetic multi-filament yarn, synthetic single filament or spun yarn.

18. The method of claim 11, further comprising cutting the at least two strips width-wise to form a mesh piece having a mesh body formed by the first knitted portion and two sets of at least two extensions, each set of at least two extensions formed by respective second knitted portions on either side of the first knitted portion or further comprising cutting the at least two strips of each second knitted portion width-wise half way between respective first knitted portions.

19. The method of claim 11, forming a biocompatible implantable mesh for use in reconstructing tissue.

20. An implantable mesh comprising:
a mesh body formed using a first knitting sequence in a machine direction, the mesh body having a width;
a first set of at least two mesh extensions extending parallel to one another in the machine direction from a first side of the mesh body, the at least two mesh extensions formed using a second knitting sequence; and
wherein the first knitting sequence comprises the following:
GB2 (3–2/3–2/3–2/3–2/3–2/3–2/3–2/3–2/3–2/3–2)//
GB3 (2–2/1–1/2–2/1–1/3–3/1–1/2–2/1–1/2–2/0–0)//
GB4 (2–2/1–1/2–2/1–1/3–3/1–1/2–2/1–1/2–2/0–0)//
GB5 (2–2/3–3/2–2/3–3/1–1/3–3/2–2/3–3/2–2/4–4)//

GB6 (2-2/3-3/2-2/3-3/1-1/3-3/2-2/3-3/2-2/4-4)//
and the second knitting sequence comprises the following:
GB2 (3-2/3-2/3-2/3-2/3-2/3-2/3-2/3-2/3-2)//
GB3 (2-2/1-1/2-2/1-1/3-3/1-1/2-2/1-1/2-2/0-0)//
GB4 (2-2/1-1/2-2/1-1/2-2/1-1/2-2/1-1/2-2/1-1)//
GB5 (2-2/3-3/2-2/3-3/1-1/3-3/2-2/3-3/2-2/4-4)//
GB6 (2-2/3-3/2-2/3-3/2-2/3-3/2-2/3-3/2-2/3-3)//
wherein the first knitting sequence is repeated at least twice to make a first knitted portion and the second knitting sequence is repeated at least twice to make a second knitted portion; and wherein the first knitting sequence and the second knitting sequence are formed continuously from a single set of textile strands.

\* \* \* \* \*